(12) United States Patent
Reinhard

(10) Patent No.: US 6,488,645 B1
(45) Date of Patent: Dec. 3, 2002

(54) SUIT FOR PROBLEMS ASSOCIATED WITH ORTHOSTASIS

(75) Inventor: Andreas Reinhard, Zollikon (CH)

(73) Assignee: Prospective Concepts AG, Zollikon (CH)

( * ) Notice: Subject to any disclaimer, the term of this patent is extended or adjusted under 35 U.S.C. 154(b) by 0 days.

(21) Appl. No.: 09/446,446

(22) PCT Filed: Apr. 23, 1998

(86) PCT No.: PCT/CH98/00162
§ 371 (c)(1),
(2), (4) Date: Apr. 18, 2000

(87) PCT Pub. No.: WO99/53876
PCT Pub. Date: Oct. 28, 1999

(30) Foreign Application Priority Data

Apr. 20, 1998 (CH) .................................................. 902/98

(51) Int. Cl.[7] .................................................. A61F 5/00
(52) U.S. Cl. ........................ 602/19; 602/5; 602/20; 602/23
(58) Field of Search ..................... 128/736, 779; 602/1, 5, 13, 29, 20, 23

(56) References Cited

U.S. PATENT DOCUMENTS 3,823,712 A * 7/1974 Morel ......................... 602/13
4,039,039 A * 8/1977 Gottfried ..................... 602/13
4,157,713 A * 6/1979 Clarey ......................... 602/13
4,938,208 A * 7/1990 Dye ............................. 602/13

* cited by examiner

Primary Examiner—Michael A. Brown
Assistant Examiner—Lalita Hamilton
(74) Attorney, Agent, or Firm—Jenkens & Gilchrist, P.C.

(57) ABSTRACT

The invention relates to a suit for problems associated with orthostasis which is comprised of a pair of trousers made of a slightly stretchable textile material. A plurality of essentially linear or wavy strips (14, 15) are inserted along the entire length of the trousers. Said strips are made of double-walled, liquid-tight, slightly stretchable textile material. The two layers of this material are connected to one another at connection points. This results in the production of cavities which are filled with a liquid. Suspenders (11) hold the trousers and are simultaneously constructed as reservoirs (12) for the liquid. In order to increase the pressure on the abdominal region, a flat bladder (13) can be placed in the trousers and, like the strips (14, 15), can be supplied with fluid from the reservoirs (12). As a result, liquid columns are produced which extend over a large portion of the body height. Said columns build up a compensating pressure on the legs and the lower abdomen. The trousers are closed by two lateral zip fasteners (21). The knees and genital region are covered by elastic inserts (16, 17). The strips (14, 15) are either essentially straight or wavy on both sides.

23 Claims, 4 Drawing Sheets

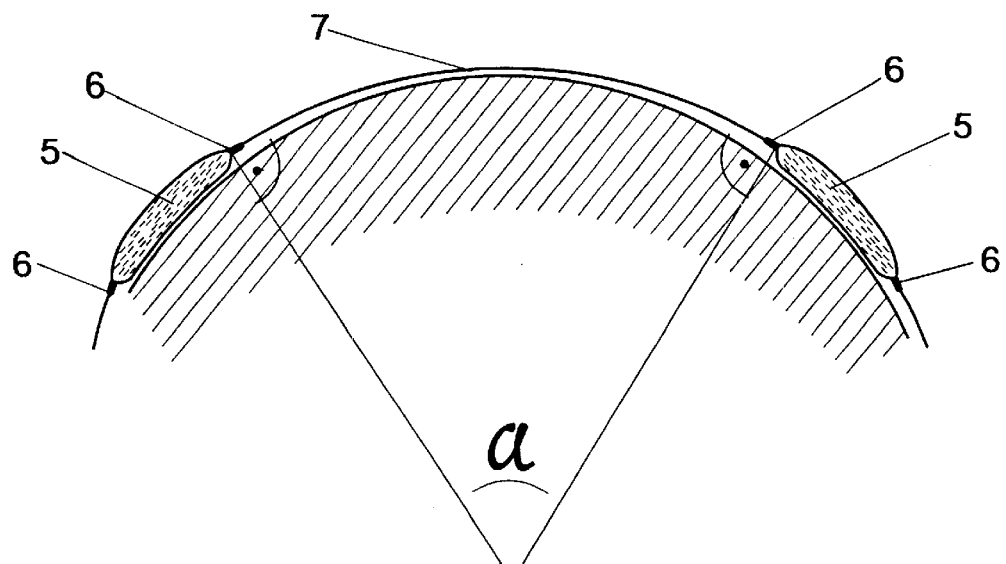
Fig. 3
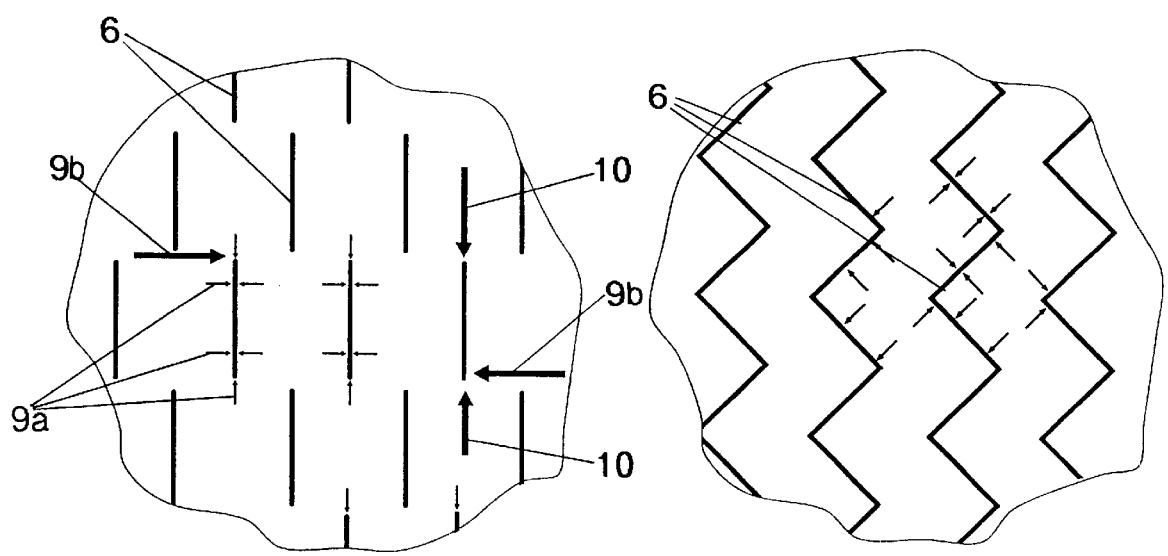
Fig. 4
Fig. 5

SUIT FOR PROBLEMS ASSOCIATED WITH ORTHOSTASIS

The present invention relates to an item of clothing for patients with orthostasis problems in accordance with the preamble to claim 1.

In patients with orthostasis syndrome of the most diverse genesis the blood stays in the regions of the legs and intestine veins in the transition from lying to standing.

In order to prevent this symptom or at least to alleviate it, so-called support stockings or trousers are known, which include elastic threads worked into them and under whose influence a pressure is exerted at least on the legs. The disadvantages of these elastic stockings or trousers lie in that they exert a pressure on the legs or the lower body even when the patient is lying, are troublesome and often only pulled on with the aid of a third party, and apart from this are only offered in fixed sizes. This allows neither room for individual body sizes outside the available sizes, nor for adjustment to instantaneous bodily conditions.

The aim of the present invention is to produce an orthostasis suit, which can be adjusted both to individual body size and also to its instantaneous value. Further the suit according to the invention can be adjusted to the strength of the current orthostasis syndrome.

The addressing of the stated aim is presented in the characterising part of claim 1 for its essential features, for further advantageous features in the claims dependent on it.

Figure 1:
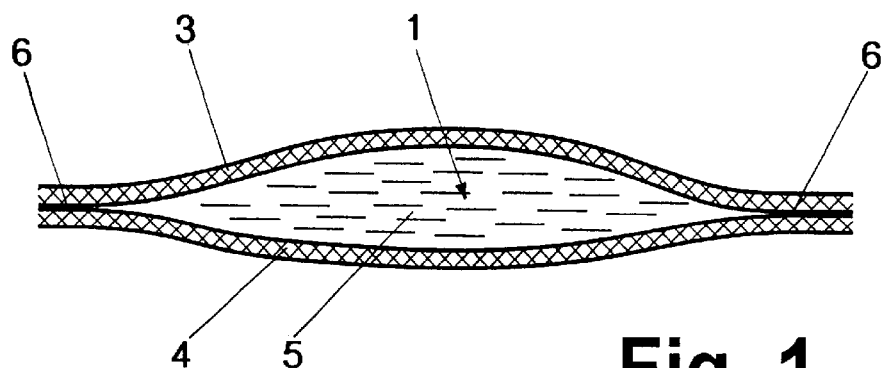
Figure 6:
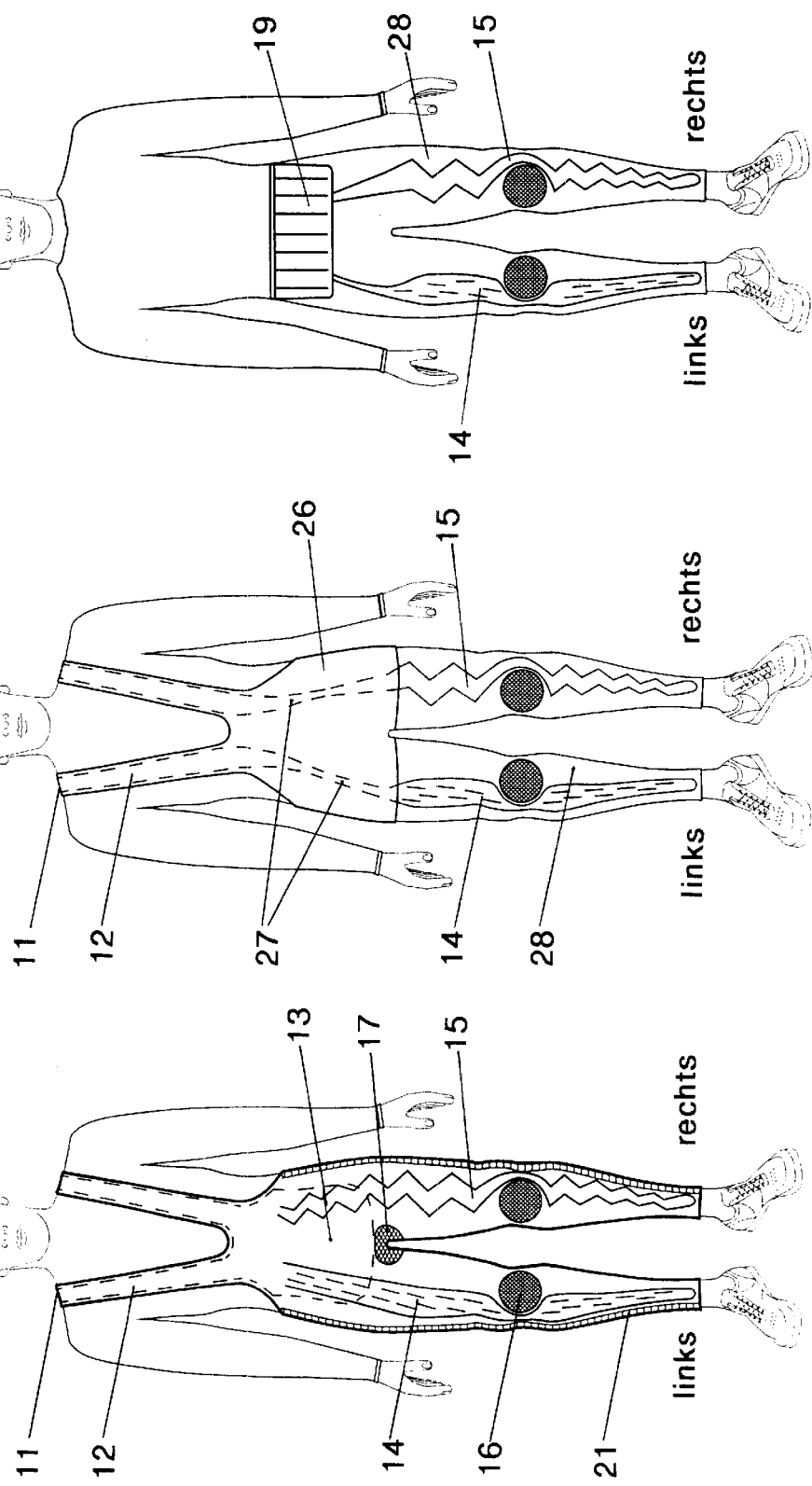
Figure 7:
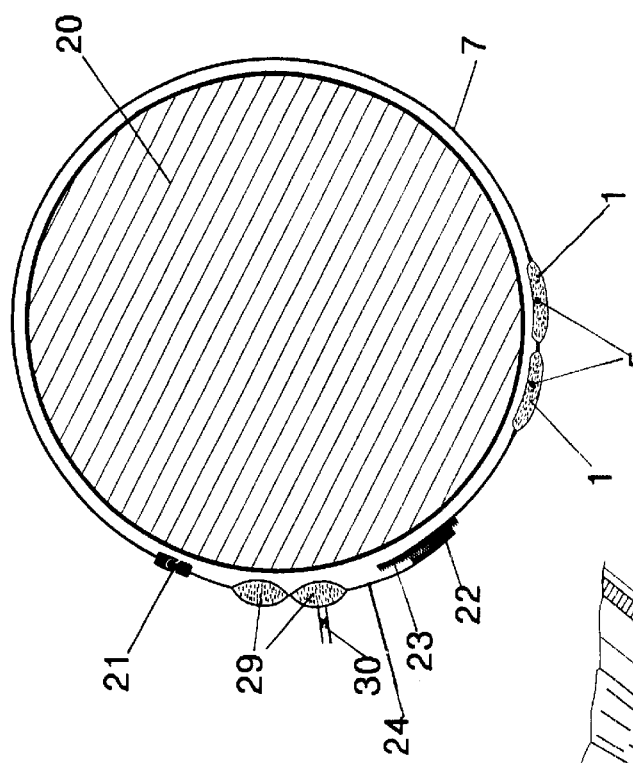
Figure 8:
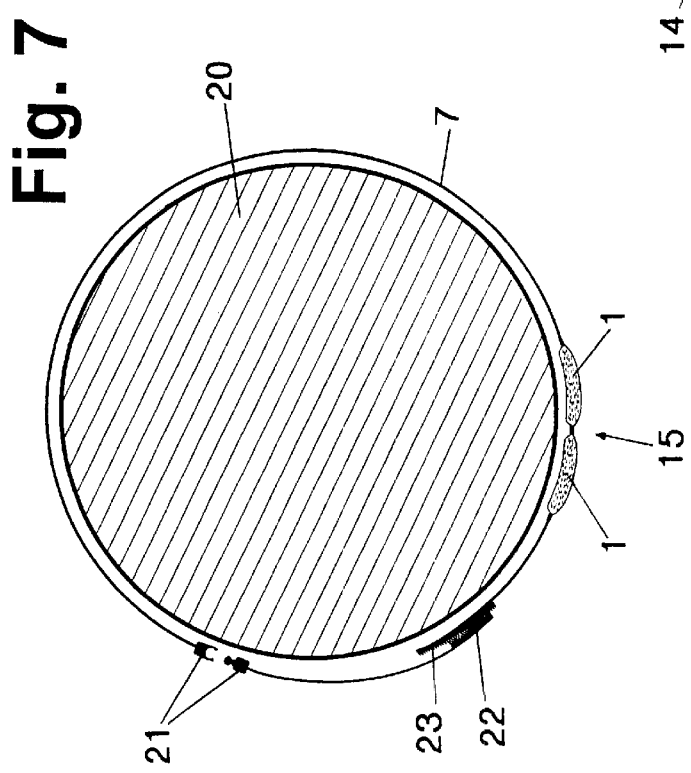
Figure 9:
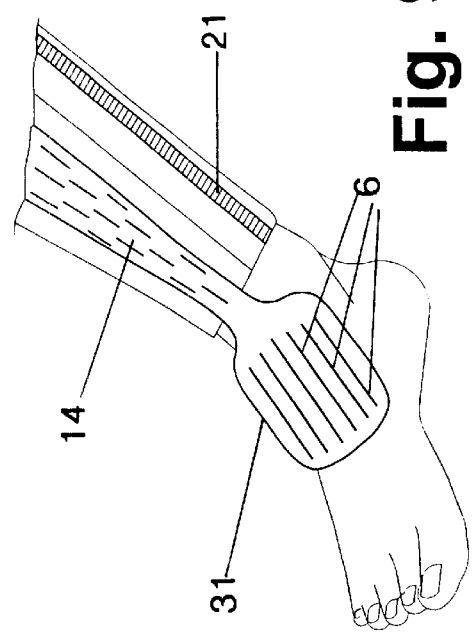

Using the enclosed drawings, the concept of the invention is more closely described by means of embodiments. Shown are:

FIG. 1 a cross section through the build up of layers of the orthostasis suit,

FIG. 2a a plan view,

FIG. 2b a first section,

FIG. 2c a second section,

FIG. 2d a third section through a first arrangement of connecting positions,

FIG. 3 a first section through a part of an orthostasis suit,

FIG. 4 a second arrangement of connecting positions,

FIG. 5 a third arrangement of connecting positions,

FIG. 6 a front view of a first embodiment of an orthostasis suit,

FIG. 7 a second cross section through a part of an orthostasis suit with closure arrangement, FIG. 8 the object of FIG. 7 with a tensioning device, FIG. 9 the view of an extension according to the invention, FIG. 10 a front view of a second embodiment of an orthostasis suit, FIG. 11 a front view of a third embodiment of an orthostasis suit.

The orthostasis suit according to the invention—comprising two socking-like elements—or constructed as trousers—is basically constructed from two different textile components: The first component is a low stretch, moisture permeable material, for instance constructed from aramid fibres; the second component, similarly of a textile nature, comprises two layers of a fluid-tight material. The two layers are joined together in places by welding, gluing or sewing with a following sealing.

FIG. 1 shows a section through these two components: it comprises an inner—that is close to the body—fluid-tight textile layer 3 and an outer layer 4 from the same material. The layers 3, 4 are joined together at connecting positions 6 by gluing, welding or sewing (with a watertight or sealed seam). There arises thereby a hollow space 5 between the layers 3, 4, which can be filled with a liquid 1. The liquid 1 can be water, which is stabilised by means of a bacteriostatic additive and possibly includes further additives to adjust the density and flowing ability.

FIGS. 2a, b, c, d shows the attachment of connection positions 6 between the layers 3, 4 in detail views. As already explained, these connecting positions 6 are produced by welding, gluing or sewing. In FIG. 2a a field of for instance six connecting positions 6 is shown schematically from a section of the protective suit. Each single connecting position has the form of a long narrow strip. A section AA according to FIG. 2b shows, that the distance between the ends of the strip-formed connecting positions 6 is shortened as soon as the fluid present in the hollow space 5 between the layers 3, 4 flows in and is put under pressure. The same applies for the lateral separation of the connecting positions 6, as is shown in the section BB according to FIG. 2c.

If now a construction formed by the layers 3, 4 is laid around, for instance, a thigh, then the result is as shown schematically in FIG. 2d:

The outer layer 4 is tensioned to a tensile force σ, the inner layer 3 lies, essentially tension-free, against the surface of the body; inside the hollow space 5 the pressure p is applied. This builds up the tensile force σ, which is transmitted over the connecting positions 6, so that a particular pressure p corresponds to a particular tensile force.

If now two—shown in the section—hollow spaces 5 are arranged such that a separating zone 7 lies between them, which does not contain a hollow space 5, then the tensile force σ is transmitted essentially without attenuation from the hollow space 5 to the hollow space 5. The attenuation of the tensile force, which normally arises with a wrapping angle α:

$$\sigma(\alpha) = \sigma_0 \cdot e^{-\alpha f_H}$$

where $\sigma_0$ = Initial tension $f_H$ = coefficient of static friction applies for rigid wrapped bodies. Human body tissue is however largely flexible and deformable.

The separation zone 7 is preferably constructed from the first component, that is a moisture-permeable low stretch textile material.

Figure 2:
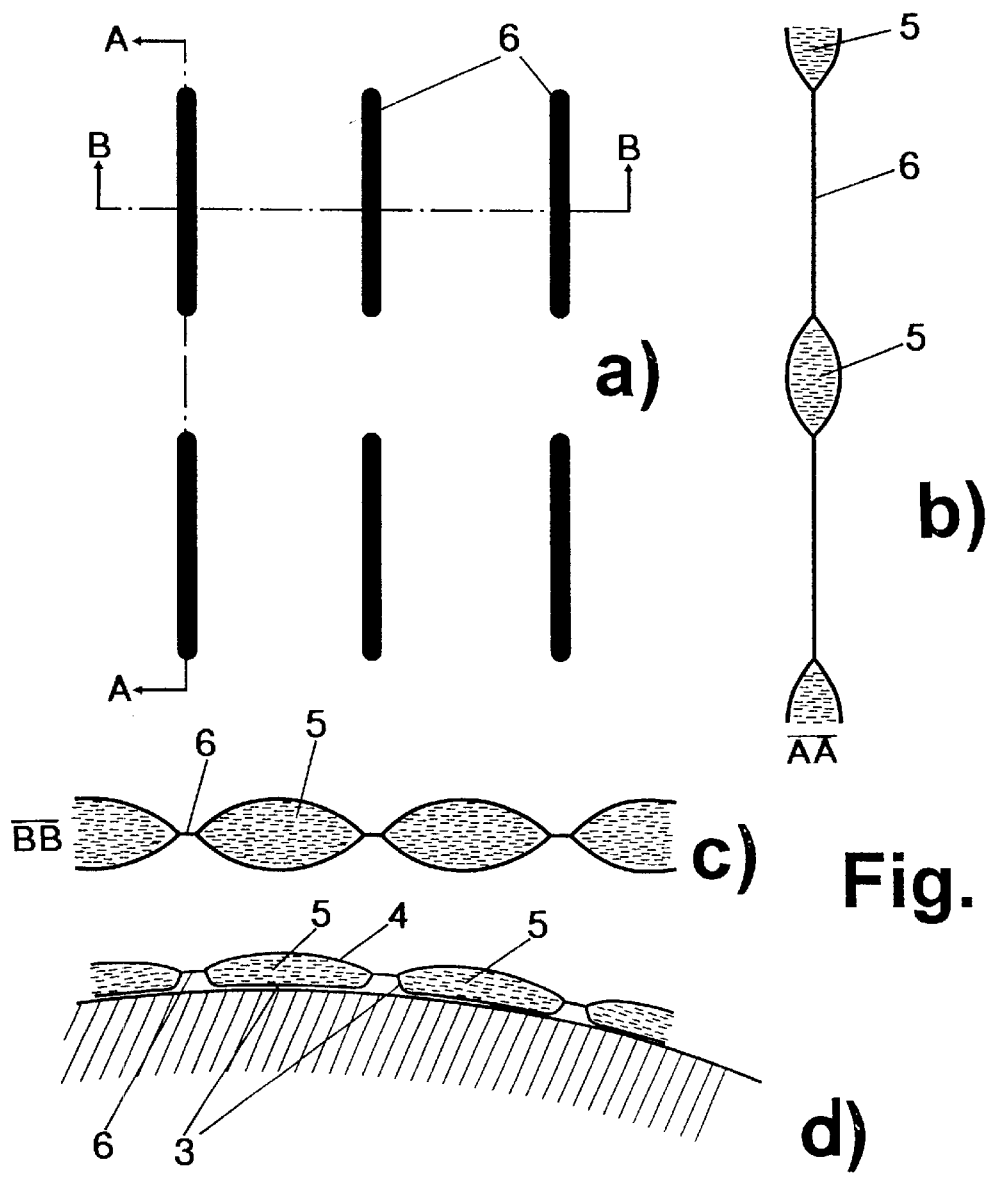

The connecting positions 6 are immediately adjacent to the hollow spaces. They can, as shown in FIGS. 1, 2, connect the layers 3, 4, or additionally effect the connection to the textile material from which the separation zone 7 is manufactured.

In FIG. 4 the linearly constructed connection positions are arranged in rows, displaced from each other. Due to the application of pressure on the fluid, which is present in the hollow spaces arising between the layers 3, 4, force effects arise on the connecting positions 6 (small arrow 9a in FIG. 4). The construction comprising the layers 3, 4 thereby shortens advantageously in the direction at right angles to the direction of the connecting positions 6 (large horizontal arrow 9b in FIG. 4). To a lesser extent a similar shortening occurs due to this arrangement, in the direction of the linear connecting positions 6 (large vertical arrow 10). The tensile forces a arising therefrom perform in the same ratio such that $\sigma_{across} > \sigma_{along}$. The fluid present between the layers 3, 4 has great mobility in this arrangement; it can flow both along and also across the direction of the linear connecting positions 6.

The arrangement according to FIG. 5, as opposed to that of FIG. 4, builds up almost isotropic tensile forces, since due to the zig-zag pattern of the connecting positions 6 the projections in both coordinate directions in the plane of the layers 3, 4 are almost exactly equally large, or at least can be equally large. Thereby an almost isotropic shrinkage results of the size of a surface piece provided with connecting positions 6 in this manner.

The mobility of the fluid in the hollow spaces 5 between the connecting positions 6 according to FIG. 5 is limited by the pattern described insofar as it is not possible at right angles to the connecting positions 6. Instead of the depicted zig-zag pattern with sharp corners, a construction with radii is included in the scope of the invention; instead of a zig-zag pattern in the narrow sense a wave shaped pattern emerges. All such constructions are included and to be understood within this scope.

FIG. 6 shows the orthostasis suit according to the invention, in a first embodiment with modifications regarding the arrangement of the connecting positions 6, shown as two half illustrations "left" and "right".

The embodiment according to FIG. 6 is produced as trousers with braces 11, which are also constructed as reservoirs 12 for the fluid 1. The fluid column creates due to gravity the pressure in the hollow spaces.

$$p = \rho g h$$

Where
p=pressure
ρ=density of the fluid
h=height difference from the upper fluid level to the position under consideration in the orthostasis suit.

Beneath the two reservoirs 12 there is a flat bladder 13 (shown dashed), which is positioned within the low-stretch textile material of the first component, which here covers the belly/abdominal region. At least two strips 14, 15, each of which carries a modification of a pattern of connecting positions 6, open from below into the bladder 13, at least at their upper edges. The strip 14, on the left, carries a pattern according to FIG. 4, the strip 15, on the right, one according to FIG. 5. Obviously in a particular production pattern the two strips 14, 15 are formed the same; they extend from the bladder 13 down to above the ankle bone. Not shown, but however included in the scope of the invention are bands 38 to 41, branched at the top or/and at the bottom. The run of the tension and the anatomical matching can thereby be optimised.

According to the degree of filling of the reservoir 12 and the density ρ of the fluid a compensating pressure is built up in standing, which essentially corresponds to the difference in blood pressure over the corresponding height difference. The compensating pressure is converted by the formation of the pattern of connecting positions 6 into a circumferential tension σ, which applies in the separation zones 7; this again builds a compensating pressure around the body parts enclosed by the orthostasis suit.

The region of the knee cap is—in order to retain normal mobility—exempted from the tensile force; an elastic textile material is provided there, in the form of round or long inserts 16. Like the knee, the genital region is similarly exempted from the tensile force. It either remains uncovered by the orthostasis suit or is similarly covered by an elastic insert 17.

Alternatively the whole knee region can essentially remain uncovered by the suit; the joining of the thigh section to the lower leg section is then provided by a preferably lateral lying strip of textile material, which includes the strip 14, or 15.

In FIG. 6 one each of the strips 14, 15 is shown. Obviously it is included in the scope of the invention, that more than one strip can be provided. On the one hand the circumference of the orthostasis suit can thereby be more strongly shortened, which somewhat increases mobility, on the other hand the necessary amount of fluid—and therewith the weight of the orthostasis suit is then also correspondingly greater.

FIG. 7 shows the closure arrangement of the orthostasis suit according to FIG. 6. The orthostasis suit, comprising above all the separation zone 7 is fitted around a schematically shown leg 20. The strip 15 (or 14) will tension this in the standing position of the wearer by build up of pressure in the fluid 1.

In order to afford the wearer of the orthostasis suit the greatest possible self sufficiency and to assure the correct functioning of the orthostasis suit, the closure device is in two parts: A velcro fastener 22, 23 serves to fit the orthostasis suit to the instantaneous bodily situation of the wearer. A zip fastener 21 serves, after the fitting is complete, to close the orthostasis suit in the lying position of the wearer. Whilst third party assistance is necessary for optimal fitting, the closure of the zip fastener 21 can be effected by the wearer alone. Additionally, the zip fastener 21 can be assembled such that it closes from above downwards; the mating together of the two parts of the zip fastener 21 can then be effected at the top, the closure in case of need with the aid of a stick, which is inserted into the closing device of the zip fastener 21. The velcro fasteners 22, 23 and the zip fastener 21 are shown both in FIG. 6 and also in FIG. 7 lying on the outside and closely adjacent. Obviously the velcro fasteners 22, 23 can be arranged proximally on the legs, and the zip fastener 21 laterally. The presence of an arrangement for fitting (for instance the velcro fasteners 22, 23) and an arrangement for closure (that is the zip fastener 21) is essential to the invention. Their spatial arrangement has to be undertaken so as to offer the wearer of the orthostasis suit the greatest possible comfort both in putting on and taking off, and also in wearing the orthostasis suit.

FIG. 8 is the illustration of a further example according to the invention. One or more airtight channels 29, constructed for instance like the strips 14 extend over the entire length of the orthostasis suit in accordance with FIG. 6, or over that of the leg sections in accordance with FIG. 11. The channels 29 are for instance arranged in the cloth 24 between the zip fastener 21 and the velcro fasteners 22, 23. Following the closure of the velcro fasteners 22, 23 and the zip fastener 21 the wearer of the orthostasis suit can apply a hand operated pump to a valve 30 and use it to inflate the channels 29 with air under pressure. Thereby a tighter fit of the orthostasis suit is effected and the zip fastener 21 can be more easily closed.

The veins running in the feet are often also affected by orthostasis syndrome. In these cases it can be helpful to include the foot region in the build up of compensating pressure. FIG. 9 shows—as a detail—this extra feature.

Onto the strips 14 or 15 a cloth 31 is connected, which for instance carries parallel connecting positions 6. This cloth is inserted into the advantageously high or half height boot, under the tongue. It is naturally a precondition that the shoe is low-stretch over the instep. Thereby the necessary circumferential tension is also built up in the shoe, due to the effect of the compensating pressure. The cloth 31 can be matched in its cutting to the anatomical features of the foot.

If the belly/abdominal region is not, or little affected by orthostasis syndrome, then this part can either be omitted, or rather advantageously, formed substantially without effectiveness. FIG. 10 shows this embodiment.

From the reservoirs 12 integrated in the braces 11 the fluid 1 passes into the strips 14, or 15 through two relatively thinly constructed channels 27.

Whilst the construction of the leg sections of the orthostasis suit is similar to that according to FIG. 6, that is from low stretch material, the upper part can be produced from pliant, advantageously synthetic textile materials. This upper section 26 has the task of retaining the leg sections 28, is a strong point for the braces 11 and keeps the channels 27 in the correct position. The degree of filling of the reservoir depends again on the number of strips 14 or 15. This embodiment can also be supplemented by a cloth 24 according to FIG. 8 in each leg. Instead of the reservoir 12 shown integrated into the braces 11 in FIG. 6 a vest-like upper section—not shown—is also in accordance with the invention, which is the carrier for a reservoir 19, which feeds both the strips 14 or 15, and also the bladder 13.

If the compensating pressure can be kept small, based on the medical indications, then the possibility exists of dispensing with the braces 11. The reservoirs 12 are then, as shown in FIG. 11, amalgamated into a single, preferably segmented reservoir 19, which is located in the belly region. Thus the maximum compensating pressure is reduced, taking the density ρ of the fluid 1 into account, to the difference in height between the reservoir 19 and the lowest position in the leg section 28.

The reservoir 19 is again connected with the strips 14, or 15 by channels 27. Here also supplementing by cloths 24 is in accordance with the invention.

A further addition according to the invention is to supplement both the upper section 26 and the belly section 28 in part or over their entire length with an elastic insert, which has the mechanical characteristics of a so-called wound back spring, that is it only reacts in an elastic manner from a predetermined, selected circumferential tension σ. These elastic inserts run force-effectively parallel to the zip fastener 21 and are for instance provided between the zip fastener 21 and the velcro fastener 22, 23 or rather along the proximal meridian of the leg sections 28.

What is claimed is:

1. An orthostasis suit for the compensation of lowered or failing capability of patients to regulate the blood pressure in the hypotonic region, especially during the change from a lying to a standing position, with regions arranged in at least two vertical strips along the parts of the body covered by the orthostasis suit, which comprise two layers of a watertight low-stretch textile material, which are joined together at connecting points and form hollow spaces, which can be filled with a fluid, with means for the closure of the orthostasis suit along the body parts covered by it, with means to fit the orthostasis suit to the present size conditions of its wearer and with means to tension the orthostasis suit, wherein the orthostasis suit simultaneously covers both at least one part of the thigh as well as at least one part of the lower leg, the orthostasis suit includes separation zones alongside the vertical strips, the connecting positions are arranged in patterns and at the edge of the strips the watertight layers join to a moisture permeable material of the separation zones, on the standing up of the wearer the fluid present in the hollow spaces essentially due to its hydrostatic pressure, can act at least in part in a compensatory manner on the blood pressure acting in the covered parts of the body, and the knee cap region of the orthostasis suit is substantially exempted from the tensile force provided by the orthostasis suit.

2. An orthostasis suit according to claim 1, further comprising a reservoir for the fluid lying above the regions having hollow spaces.

3. An orthostasis suit according to one of the claims 1 to 2, wherein the connecting positions are in straight lines which run essentially parallel to each other, whose length corresponds somewhat to their lateral separation, the individual connecting positions lie essentially on two sets of parallel lines, which are displaced by about half of the lateral separation of two adjacent connecting positions.

4. An orthostasis suit according to one of the claims 1 to 2; wherein the regions carrying hollow spaces are arranged in strips, which extend over the whole length of the orthostasis suit.

5. An orthostasis suit according to claim 4, wherein the strips are essentially straight.

6. An orthostasis suit according to claim 4, wherein the strips are zig-zag shaped.

7. An orthostasis suit according to claim 1, further comprising an upper part of the orthostasis suit, adapted to cover at least a part of the trunk.

8. An orthostasis suit according to claim 7, wherein the upper part of the orthostasis suit covers at least the belly/abdominal region, the upper part of the orthostasis suit has a flat bladder, which is arranged inside the orthostasis suit in the belly/abdominal region and can be joined to the orthostasis suit.

9. An orthostasis suit according to claim 7, further comprising a belt with a reservoir, which can be joined to the orthostasis suit.

10. An orthostasis suit according to claim 7, wherein the upper part of the orthostasis suit has braces.

11. An orthostasis suit according to claim 10, further comprising a reservoir worked into the braces.

12. An orthostasis suit according to claim 1, further comprising elastic inserts running lengthwise.

13. An orthostasis suit according to one of the claims 1 to 2, wherein the means for closure comprise a zip fastener for each leg.

14. An orthostasis suit according to claim 13, wherein the means for tensioning comprise channels along the length of the orthostasis suit and arranged in the cloth between the zip fastener and the hook and loop means, which can be inflated with compressed air and thereby can create a circumferential pressure corresponding to the least pressure provided in the orthostasis suit.

15. An orthostasis suit according to one of the claims 1 to 2, wherein the means for fitting comprise a hook and loop means for each leg, whereby one part of the hook and loop means fastened to a cloth, the other part is fastened to the part of the orthostasis suit enclosing the body.

16. An orthostasis suit according to claim 15, wherein the means for tensioning comprise channels along the length of the orthostasis suit and arranged in the cloth between the zip fastener and the hook and loop means, which can be inflated with compressed air and thereby can create a circumferential pressure corresponding to the least pressure provided in the orthostasis suit.

17. An orthostasis suit according to claim 1, wherein at the lower end of the strips a cloth is fastened, which has the same construction as the strips, is similarly filled with the same fluid as the strips, and the hollow spaces of the strips and the cloth communicate, whereby the cloth is inserted as a tongue in the shoe of the wearer and can be fixed on the foot with the normal closure device of the shoe.

18. An orthostasis suit according to claim 1, wherein the strips can be branched.

19. An orthostasis suit according to claim 18, characterised in that the means for closure comprise a zip fastener (21) for each leg.

20. An orthostasis suit according to claim 18, characterized in that the means for fitting comprise a hook and loop fastener (22, 23) for each leg, whereby one part of the velcro fastener (22) is fastened to a cloth (24), the other part (23) to the part of the orthostasis suit enclosing the body.

21. An orthostasis suit according to claims 18, 19 and 20 characterised in that the means for fitting closing, and tensioning comprise channels (29) along the length of the orthostasis suit and arranged in the cloth (24) between the zip fastener (21) and the hook and loop fastener (22), which can be inflated with compressed air and thereby can create a circumferential pressure corresponding to the least pressure provided in the orthostasis suit.

22. An orthostasis suit according to claim 1, 2 or 4, characterised in that at the lower end of the strips (14, 15) a cloth (31) is fastened, which has the same construction as the strips (14, 15), is similarly filled with the same fluid as them, and that the hollow spaces (5) of the strips (14, 15) and the cloth (31) communicate, whereby the cloth (31) is inserted as a tongue in the shoe of the wearer and can be fixed on the foot with the normal closure device of the shoe.

23. An orthostasis suit according to claim 1, characterised in that the strips (14, 15) can be branched.

\* \* \* \* \*

UNITED STATES PATENT AND TRADEMARK OFFICE
CERTIFICATE OF CORRECTION

PATENT NO. : 6,488,645 B1
DATED : December 3, 2002
INVENTOR(S) : Andreas Reinhard It is certified that error appears in the above-identified patent and that said Letters Patent is hereby corrected as shown below:

Title page,
Item [54], Title, replace "SUIT FOR PROBLEMS ASSOCIATED WITH ORTHOSTASIS" with -- ORTHOSTASIS SUIT --

Column 6,
Line 13, replace "2; wherein" with -- 2, wherein --
Line 52, replace "means fastened" with -- means is fastened --

Column 7, lines 3-15 through Column 8, lines 1-13,
Delete

```
19. An orthostasis suit
according to claim 18, characterised in that the means for
closure comprise a zip fastener (21) for each leg.

20. An orthostasis suit according to claim 18, characterized
in that the means for fitting comprise a hook and loop
fastener (22,23) for each leg, whereby one part of the velcro
fastener (22) is fastened to a cloth (24), the other part(23)
to the part of the orthostasis suit enclosing the body.
```

```
21. An orthostasis suit according to claims 18, 19 and 20
characterised in that the means for fitting closing, and
tensioning comprise channels (29) along the length of the
orthostasis suit and arranged in the cloth (24) between the
zip fastener (21) and the hook and loop fastener (22), which
can be inflated with compressed air and thereby can create a
circumferential pressure corresponding to the least pressure
provided in the orthostasis suit.

22. An orthostasis suit acording to claim 1, 2 or 4,
characterised in that at the lower end of the strips (14, 15)
a cloth (31) is fastened, which has the same construction as
the strips (14,15), is similarly filled with the same fluid as
them, and that the hollow spaces (5) of the strips (14, 15)
and the cloth (31) communicate, whereby the cloth (31) is
inserted as a tongue in the shoe of the wearer and can be
fixed on the foot with the normal closure device of the shoe.
```

UNITED STATES PATENT AND TRADEMARK OFFICE
CERTIFICATE OF CORRECTION

PATENT NO. : 6,488,645 B1
DATED : December 3, 2002
INVENTOR(S) : Andreas Reinhard It is certified that error appears in the above-identified patent and that said Letters Patent is hereby corrected as shown below:

Column 7, lines 3-15 through Column 8, lines 1-13 (cont'd),

```
23. An orthostasis suit according to claim 1, characterised in
that the strips (14, 15) can be branched.
```

Signed and Sealed this

Seventeenth Day of August, 2004

JON W. DUDAS
*Acting Director of the United States Patent and Trademark Office*